(12) United States Patent
Kuehni et al.

(10) Patent No.: US 9,352,865 B2
(45) Date of Patent: *May 31, 2016

(54) DEVICES AND METHODS FOR FILLING A FLEXIBLE LIQUID MEDICAMENT CONTAINER WITH LIQUID FROM A LIQUID MEDICAMENT RESERVOIR

(71) Applicant: Roche Diagnostics International AG, Rotkreuz (CH)

(72) Inventors: Florian Kuehni, Wabern (CH); Christoph Huwiler, Baar (CH); Martin Wyss, Burgdorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 288 days.

This patent is subject to a terminal disclaimer.

(21) Appl. No.: 14/072,014

(22) Filed: Nov. 5, 2013

(65) Prior Publication Data

US 2014/0090746 A1    Apr. 3, 2014

Related U.S. Application Data

(63) Continuation of application No. 12/792,138, filed on Jun. 2, 2010, now Pat. No. 8,602,067.

(30) Foreign Application Priority Data

Jun. 2, 2009  (EP) .................................... 09007303

(51) Int. Cl.
*B65B 31/02* (2006.01)
*A61J 1/20* (2006.01)
(Continued)

(52) U.S. Cl.
CPC ................ *B65B 31/025* (2013.01); *A61J 1/20* (2013.01); *A61M 5/14216* (2013.01); *A61J 1/10* (2013.01); *A61M 2209/045* (2013.01)

(58) Field of Classification Search
CPC ............ B65B 31/025; A61M 5/14216; A61M 2209/045
USPC ............. 141/7, 10, 25–27, 65, 114, 285, 301, 141/329, 330
See application file for complete search history.

(56) References Cited

U.S. PATENT DOCUMENTS 2,982,447 A    5/1961   Austin
3,911,972 A    10/1975  Huebers et al.
(Continued)

FOREIGN PATENT DOCUMENTS

EP    1820485 A1    8/2007
EP    1952837 A1    8/2008
(Continued)

OTHER PUBLICATIONS

International Search Report pertaining to Application No. PCT/EP2009007303.2-1257 dated Nov. 12, 2009, 6 pages.

*Primary Examiner* — Timothy L Maust
(74) *Attorney, Agent, or Firm* — Dinsmore & Shohl LLP

(57) ABSTRACT

A device for filling a flexible container and a method thereof are disclosed. The device may include a pressurizing chamber and an evacuation chamber. A first displacement piston is sealingly and slideably arranged within the pressurizing chamber to define an inner volume within the pressurizing chamber that is fluidly connected to a pressurizing conduit. A second displacement piston is sealingly and slideably arranged within the evacuation chamber to define an inner volume within the evacuation chamber that is fluidly connected to an evacuation conduit. A reservoir adapter is fluidly connected to the pressurizing conduit and connects to a liquid reservoir. A container adapter is fluidly connected to the evacuation conduit and connects with a flexible container. A transfer conduit is fluidly connected to the reservoir adapter and the container adapter. A valve fluidly connects the container adapter to the evacuation conduit or the transfer conduit.

20 Claims, 6 Drawing Sheets

(51) Int. Cl.
*A61M 5/142* (2006.01)
*A61J 1/10* (2006.01)

(56) References Cited

U.S. PATENT DOCUMENTS

| | | | |
|---|---|---|---|
| 4,555,221 A | 11/1985 | DuBois | |
| 4,684,365 A | 8/1987 | Reinicke | |
| 4,817,687 A | 4/1989 | Loefgren et al. | |
| 4,832,096 A | 5/1989 | Kohlbach | |
| 5,555,920 A * | 9/1996 | Godolphin | A61J 1/2089 141/130 |
| 6,202,708 B1 * | 3/2001 | Bynum | A61M 5/1409 141/105 |
| 6,585,007 B2 | 7/2003 | Kubokawa | |
| 7,959,715 B2 | 6/2011 | Kavazov et al. | |
| 7,976,505 B2 | 7/2011 | Hines et al. | |
| 8,602,067 B2 * | 12/2013 | Kuhni | A61J 1/20 141/114 |
| 2002/0128628 A1 | 9/2002 | Fathallah | |
| 2012/0059349 A1 * | 3/2012 | Kuo | A61M 5/1407 604/500 |

FOREIGN PATENT DOCUMENTS

| | | |
|---|---|---|
| FR | 8 120 E | 11/1907 |
| WO | 0238957 A1 | 5/2002 |
| WO | 2004009162 A1 | 1/2004 |
| WO | 2008122135 A1 | 10/2008 |

* cited by examiner

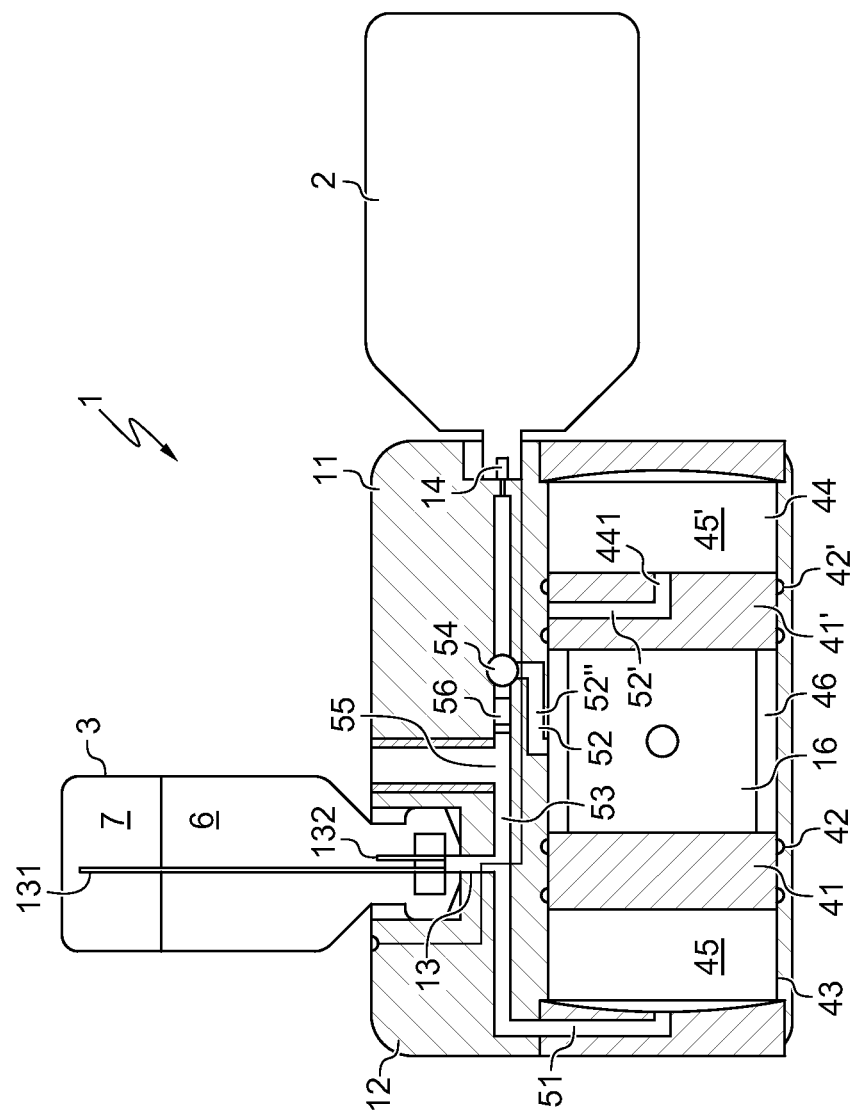

DEVICES AND METHODS FOR FILLING A FLEXIBLE LIQUID MEDICAMENT CONTAINER WITH LIQUID FROM A LIQUID MEDICAMENT RESERVOIR

CROSS REFERENCE TO RELATED APPLICATIONS

The present application is a continuation of pending U.S. patent application Ser. No. 12/792,138, filed Jun. 2, 2010, which claims priority to European Patent Application No. EP09007303.2 filed Jun. 2, 2009, which is herein incorporated by reference in its entirety.

TECHNICAL FIELD

The embodiments described herein relate to devices for filling flexible containers for storing liquid medicaments administered to patients by infusion pump devices, and methods for filling flexible containers.

BACKGROUND

Devices for the automated release of liquid medicaments are normally used with patients who have a continuous variable need of a medicine that can be administered by subcutaneous infusion. Specific applications are, for example, certain pain therapies and the treatment of diabetes, in which computer controlled infusion pump devices are used, such as insulin pumps. Such devices can be carried by a patient on the body, and contain a certain amount of liquid medicament in a reservoir in the form of a container. The medicine reservoir often comprises medicine sufficient for one or more days. The liquid medicament is supplied to the patient's body from the reservoir by subcutaneous infusion of injection, through an infusion cannula or an injection needle.

In self-administration of liquid medicaments, such as the self-administration of insulin, the patients administering by means of an infusion pump are increasingly emphasizing convenience and discretion. As a consequence such infusion devices are designed to be small to increase discretion and improve patient comfort.

While there are fully or partly disposable single-use infusion pump devices, such devices are typically non-disposable and are loaded with a disposable drug cartridge. Disposable cartridges are preferable for sterility and contamination prevention reasons. They may be delivered pre-filled with a certain liquid medicament, or empty, which are self-filled by a user. The self-filled containers may be filled with medicaments that are not available in pre-filled containers. For example, some medicaments have limited availability in pre-filled containers due to a lack of stability in liquid form when stored in plastic containers.

One common type of infusion pump device that is carried on or near the body has a medicine reservoir with a cylindrical ampoule and a displacement piston, which is pushed into the ampoule by a piston rod or threaded spindle in order to convey the liquid medicament. These known designs have the disadvantage of being longer and/or thicker than desired.

Manufacturers may meet the demand for small infusion pump devices in various ways. For example, the cylindrical ampoule may be replaced by a container with a rectangular or another suitable cross-section that interacts with a displacement piston of a corresponding shape. Embodiments of such small infusion pump devices are shown in WO 2008/122135 A1.

A further approach to meet the demand for small infusion pump devices may include replacing a syringe-type dosing mechanism, in which a piston is displaced along a long container axis by an actuator in order to convey an appropriate amount of liquid medicine, with a downstream pump system. In a downstream pump system device a miniaturized pump is arranged downstream of the reservoir and causes a suction pressure that conveys the liquid medicine from the reservoir to its destination. An example for such a pump is described in WO 2004/009162 A1.

The reservoir for a downstream pump system may be a flexible container. Such a flexible container may comprise, for example, two flexible wall sheets that are sealed together. Flexible containers have the advantage of a smaller volume surplus of the container in relation to its content, which reduces the manufacture costs and the achievable dimensions of an infusion pump device using such a flexible container. The volume of some flexible containers may be up to about 10 ml, for example. Medication for diabetes therapy is commonly available in volumes of about 1.5 ml to about 3.5 ml. Other types of therapies, e.g. pain therapy, may require other administration regimes. Therefore, other volume ranges may be more common.

One known problem with flexible containers is residual air within the container. For example, a flexible self-filled container may be provided empty and manually filled with an appropriate liquid medicament. After the flexible container is filled, residual air may persist in the flexible container. If the residual air remains in the container or in the fluidic system of a pump system, it may be administered in place of the liquid medicament, which leads to potentially dangerous dosing errors. Furthermore, the administration of air into a patient's body should generally be avoided for medical reasons.

Yet another issue with residual air present in the fluidic system of an infusion pump device is the reduced stiffness of the fluidic system. Due to the high compressibility of gases such as air in relation to liquids such as water, it becomes difficult to measure the exact pressure in the fluidic system. This impedes the detection of blockages or occlusions in the fluidic system of an infusion pump device by measuring the fluidic pressure.

Known may help a user to fill a container for infusion pump systems. However, the known devices are for use with syringe/ampoule type infusion pump systems, and cannot be properly used with flexible containers. Such filling devices are disclosed, among others, in EP 1952837 A1 and EP 1820485 A1.

SUMMARY

According to one embodiment, a device for filling a flexible liquid medicament container with a liquid from a liquid medicament reservoir may include a pressurizing chamber and an evacuation chamber. A first displacement piston is sealingly and slideably arranged within the pressurizing chamber. The first displacement piston defines a first inner volume within the pressurizing chamber. A second displacement piston is sealingly and slideably arranged within the evacuation chamber. The second displacement piston defines a second inner volume within the evacuation chamber. A pressurizing conduit is fluidly connected to the first inner volume of the pressurizing chamber. A reservoir adapter is fluidly connected to the pressurizing conduit, and to which connects a liquid reservoir. An evacuation conduit is fluidly connected to the second inner volume of the evacuation chamber. A container adapter is fluidly connected to the evacuation conduit and to which connects a flexible container.

A transfer conduit is fluidly connected to the reservoir adapter and the container adapter. A valve fluidly connects the container adapter to either the evacuation conduit or the transfer conduit.

In another embodiment, a method for filling a flexible liquid medicament container with a liquid from a liquid medicament reservoir may include: evacuating a flexible container; pressurizing a liquid reservoir; and transferring a liquid from the liquid reservoir to the flexible container with a pressure difference between the liquid reservoir and the flexible container.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 6 schematically depicts a cross-section of a device for filling a flexible container according to one or more embodiments shown and described herein.

DETAILED DESCRIPTION

Figure 1:
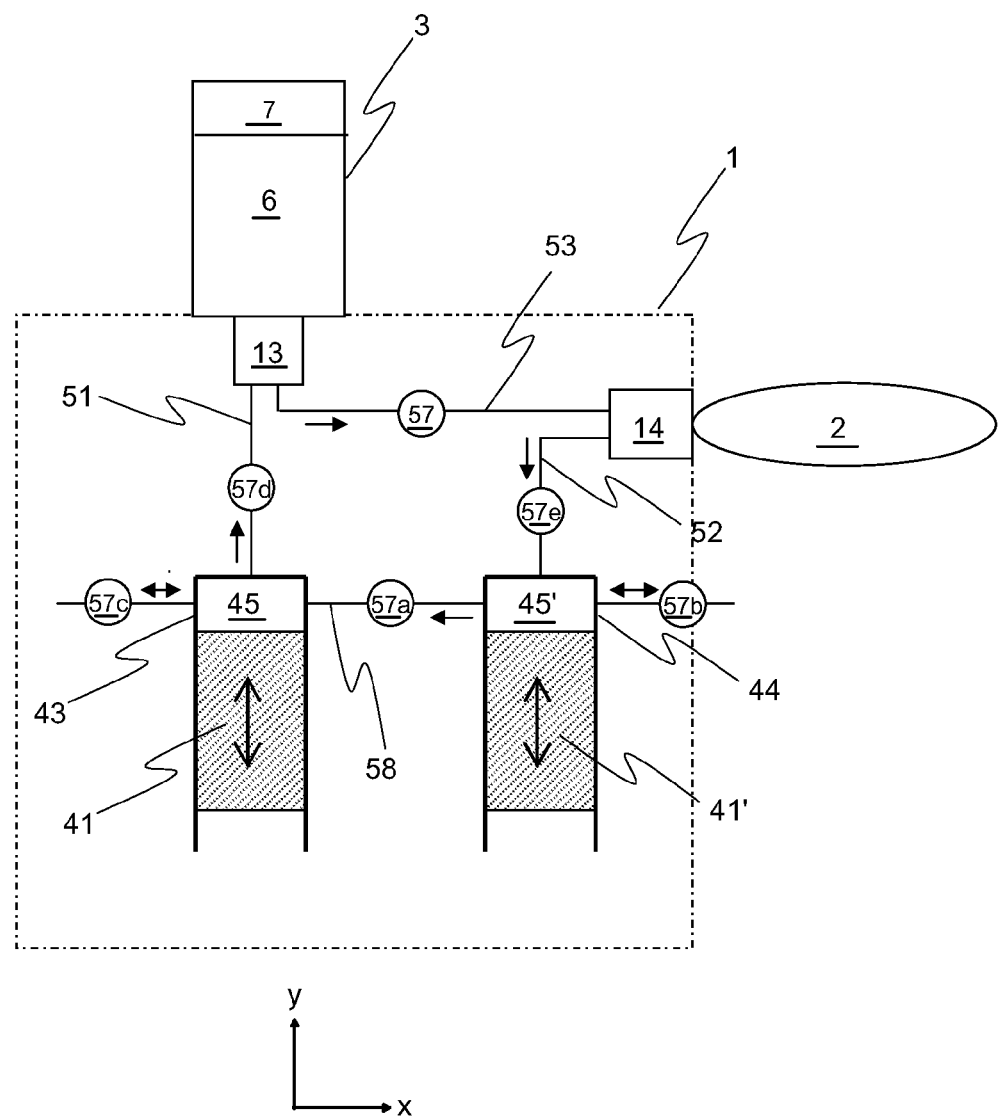
FIG. 1 schematically depicts a device for filling a flexible container according to one or more embodiments shown and described herein.

One embodiment described herein provides a device for filling a flexible liquid medicament container with a liquid from a liquid medicament reservoir. The device may facilitate the filling of a flexible container with a liquid medicament by a user.

Another embodiment described herein provides a device for filling a flexible container with a liquid from a reservoir that removes air present in the flexible container from prior to the filling of the flexible container.

Yet another embodiment described herein comprises a device for filling a flexible container with a liquid from a reservoir that prevents the entry of air bubbles into the flexible container.

A further embodiments described herein include methods for filling a flexible container, for example, a flexible container for use in an infusion pump device, with a liquid from a reservoir.

In one embodiment, a flexible liquid medicament container, such as a collapsible container, is evacuated prior to being filled with a liquid medicament in order to avoid the presence of air in the container. The evacuation may reduce the volume of air remaining in the container such as, the air in the dead volume of said container and facilitate the filling of the container. The liquid is transferred from a primary reservoir to the container by a temporarily generated pressure difference between the primary reservoir and the container.

In another embodiment, a device for filling a flexible liquid medicament container with a liquid from a liquid medicament reservoir comprises a pressurizing chamber, a displacement piston sealingly and slideably arranged in the pressurizing chamber, an evacuation chamber, and a displacement piston sealingly and slideably arranged in the evacuation chamber. Each chamber with its corresponding displacement piston defines an inner volume of the chamber. A pressurizing conduit is arranged to fluidly connect the inner volume of the pressurizing chamber with a reservoir adapter arranged to be connected to the liquid reservoir. An evacuation conduit is arranged to fluidly connect the inner volume of the evacuation chamber with a container adapter arranged to be connected with the flexible container. A transfer conduit is arranged to fluidly connect the reservoir adapter with the container adapter. A valve such as, for example, a multi-way valve, is arranged to connect the container adapter with either the evacuation conduit or the transfer conduit.

The movements of the two displacement pistons may be coupled. For example, the movements of the two displacement pistons can be coupled, such that when one displacement piston is shifted, the inner volume of a corresponding chamber is decreased, the other displacement piston is shifted, the inner volume of the other chamber corresponding to the other displacement piston is increased, and vice versa.

In a further embodiment of the device, only one stroke of the displacement pistons is sufficient to fill the flexible container. For example, the coupling mechanism between the pistons and the dimensions of the chambers and the pistons may be designed to fill the flexible container with a single stroke.

In further embodiments, the two chambers may be formed in one closed cylinder. The two displacement pistons can be formed as one single displacement piston or as two rigidly connected displacement pistons arranged in the cylinder, which divides the cylinder into the two distinct chambers. The one single displacement piston and/or the two rigidly connected displacement pistons are displaceable along a longitudinal axis of the cylinder.

According to the embodiments described herein, the device may comprise two subunits. In one embodiment, a first subunit comprises the reservoir adapter, the container adapter and the transfer conduit. A second subunit comprises the two chambers and displacement pistons. The first subunit is detachable from the second subunit.

In one embodiment of the device, the reservoir adapter and/or the container adapter for connection with the liquid reservoir are detachable from the rest of the device.

In another embodiment, the reservoir adapter comprises two parallel hollow needles or pins that are arranged to penetrate a septum of a liquid reservoir such as, for example a vial. A first needle or pin is in fluidic communication with the pressurizing conduit, and a second needle or pin is in fluidic communication with the evacuation conduit. Additionally, the first needle or pin may be substantially longer than the second needle or pin.

Embodiments of the device described herein comprise a degassing membrane, arranged to remove gas such as, air, from the transfer conduit between the reservoir adapter and the container adapter. Additionally, a bubble trap or a bubble filter, and/or a check valve, and/or a capillary segment or flow restrictor may be arranged in the transfer conduit between the reservoir adapter and the container adapter.

In yet another embodiment of the device, the pressurizing conduit and/or the evacuation conduit comprise a gate valve for temporarily interrupting the corresponding conduit, dependent upon the position of the displacement piston within the corresponding chamber.

In the embodiments described herein, the gate valve may be divided into two segments. A first segment is located in the structure of the device, and a second segment is located in the corresponding displacement piston. The position of the displacement piston within the corresponding chamber determines whether the cross-sections of the two segments overlap and fluidly connect the two segments, or the two segments do not overlap and implement the gate valve. In other embodiments, the segment of the pressurizing and/or the evacuation conduit may be located within the displacement piston ends in an outlet located on the front face of the corresponding displacement piston, facing toward the inner volume.

According to the embodiments described herein, the displacement pistons may be manually operated.

In one embodiment, the multi-way valve may be actuated by a movement of one or both displacement pistons, by the movement of an actuation mechanism or actuator for the displacement pistons, by a locking mechanism for the displacement pistons, or combinations thereof.

Devices according to the embodiments disclosed herein, may be used for filling a flexible container for use in an infusion pump device.

In a method for filling a flexible container with a liquid from a reservoir, according to the embodiments disclosed herein, the flexible container is evacuated, and the liquid reservoir is pressurized. The liquid is transferred from the liquid reservoir to the flexible container, driven by a pressure difference between the liquid reservoir and the flexible container. It is noted that, any portion of the method described above may occur in any sequence or simultaneously with any other portion of the method.

In a further embodiment of the method, the flexible container is evacuated by decreasing the inner volume of a pressurizing chamber connected to the liquid reservoir. The flexible container may also be evacuated by increasing the inner volume of an evacuation chamber connected to the flexible container.

As used herein, the terms "medicament" and "liquid medicament" are meant to encompass any drug-containing flowable medicine, therapeutic liquid or diagnostic liquid that are capable of being passed through a delivery element such as, for example, a hollow needle in a controlled manner, such as a liquid, solution, gel, fine suspension, and the like. Representative drugs include pharmaceuticals such as, but not limited to, insulin preparations ready for administration, peptides, proteins, hormones, biologically derived or active agents, hormonal and gene based agents, nutritional formulas and other substances in both solid (dispensed) or liquid form.

As used herein, the terms "subcutaneous infusion" and "subcutaneous injection" means the insertion of a needle device to a selected site within the body of a patient for intravenous, intramuscular or intradermal delivery of a liquid medicament to a subject. Further, the term needle, as used herein, means a piercing member adapted to be introduced into or through the skin of a subject such as, for example, an array of micro needles, a cannula, a hypodermic needle, and the like.

A device 1 for filling a flexible container 2 according to the embodiments described herein is schematically depicted in FIG. 1. The device 1 generally comprises a pressurizing chamber 43, with a movable displacement piston 41 sealingly closing the pressurizing chamber 43, and defining an inner volume 45 of the pressurizing chamber 43. In one embodiment, the inner volume 45 is fluidly connected via a pressurizing conduit 51 to a reservoir adapter 13. The reservoir adapter 13 can be connected to a liquid reservoir 3 such as, for example, a vial containing a liquid medicament. When the displacement piston 41 is moved into the pressurizing chamber 43 (depicted in FIG. 1 as the positive y direction), the inner volume 45 of the pressurizing chamber 43 is decreased and an increased pressure is transferred from the pressurizing chamber 43 to the interior of the liquid reservoir 3.

The device 1 may also comprise an evacuation chamber 44 with a movable displacement piston 41'. The displacement piston 41' sealingly closes the evacuation chamber 44 and defines an inner volume 45'. The inner volume 45' is fluidly connected via an evacuation conduit 52 to a container adapter 14. The container adapter 14 can be fluidly connected to a flexible container 2, which then may be filled with the liquid 6 in the liquid reservoir 3. When the displacement piston 41' is moved out of the evacuation chamber 44 (depicted in FIG. 1 as the negative y direction), the inner volume 45 of the evacuation chamber is increased and the pressure is decreased within the evacuation chamber 44. As a result of the decrease in pressure, air in the flexible container 2 and/or the container adapter 14 is sucked into the evacuation chamber 44. Thusly, the flexible container 2 is evacuated. The flexible container 2 may also be deflated by the evacuation chamber 44 in a similar fashion prior to evacuation.

The adapters 13, 14 may be fluidly connected via a transfer conduit 53 to transfer liquid 6 from the liquid reservoir 3 to the flexible container 2. In one embodiment, the evacuation conduit 52 is temporarily interrupted after the flexible container has been evacuated by, for example, closing a valve 57e arranged in evacuation conduit 52. Then the previously closed transfer conduit 53 is temporarily opened by, for example, opening a valve 57 arranged in the transfer conduit 53. After manipulating properly positioning the valves 57e, 57, liquid 6 is flowed from the pressurized liquid reservoir 3 to the flexible container 2. In another embodiment, a valve 57d that may close the pressurizing conduit 51 after pressurizing the liquid reservoir 3 can be mounted in the pressurizing conduit 51.

In another embodiment of the device 1, the chambers 43, 44 are fluidly connected via a conduit 58 with valve 57a. The valve 57a can be used to partially compensate for the pressure difference between the two chambers 43, 44 or to transfer air between the chambers 43, 44. For example, air may be transferred between the chambers 43, 44 when the displacement pistons 41, 41' are moved to their original positions in order to reset the device. In further embodiments, a conduit with a valve 57b may be fluidly connected to the evacuation chamber 44 and a valve 57c may be fluidly connected to the pressurizing chamber 43 to control the pressure difference between the chambers 43, 44 and the ambient conditions outside the device 1.

In an embodiment of a device 1 according to the present disclosure, the movement of the displacement pistons 41, 41' is mechanically coupled. The movement is mechanically coupled such that a movement of the displacement piston 41 is coordinated with a movement of the displacement piston 41'. For example, the displacement pistons 41, 41' may move in opposite directions, i.e. the displacement piston 41 moves in (positive y direction) to decrease the inner volume 45 of the pressurizing chamber 43 when the displacement piston 41' moves out (negative y direction) of the evacuation chamber 44 to decrease the inner volume 45' of the evacuation chamber 44, and vice versa.

Figure 2:
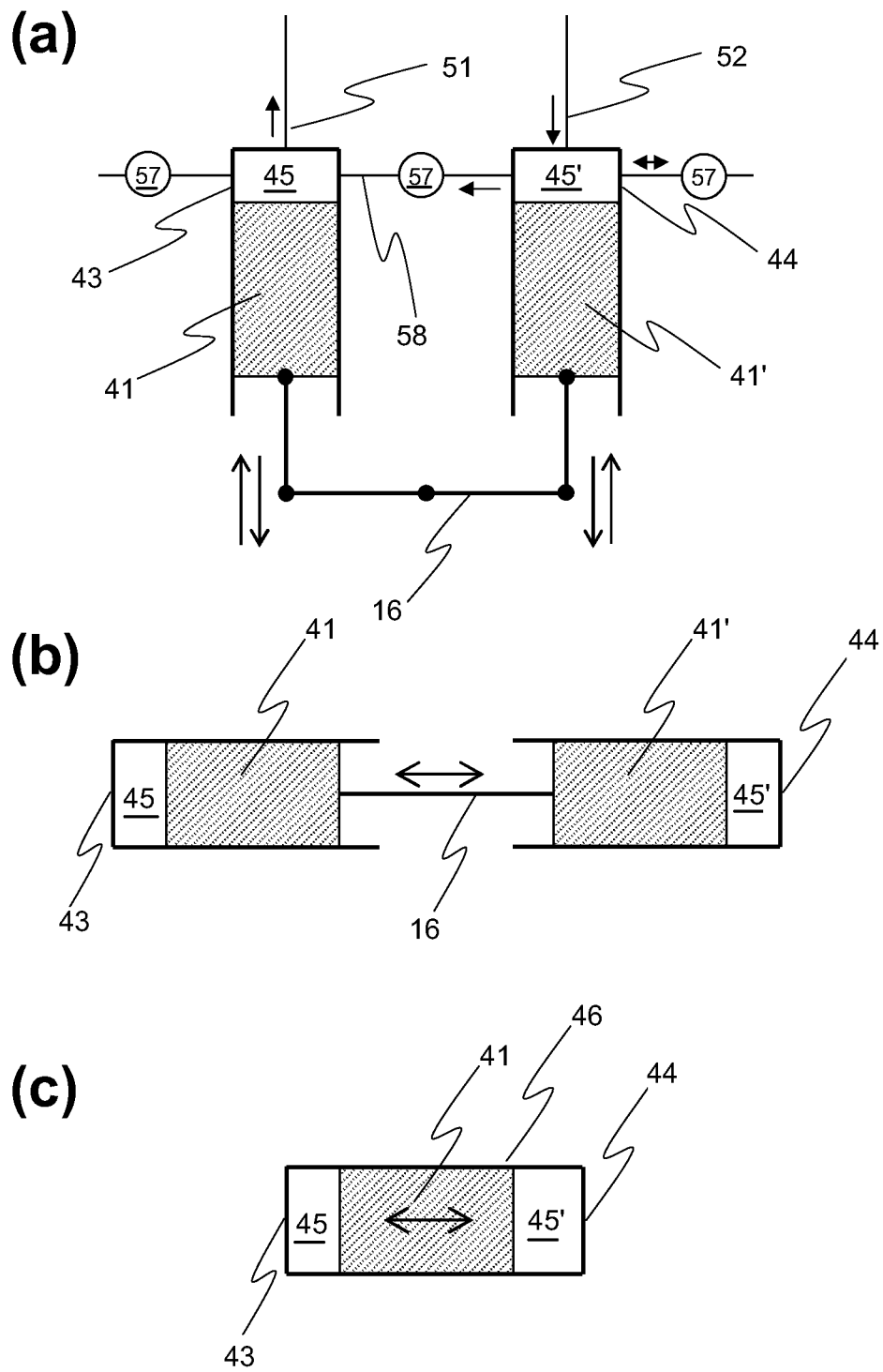
FIG. 2A schematically depicts a mechanical coupling between the two displacement pistons in a device according to one or more embodiments shown and described herein.
FIG. 2B schematically depicts a mechanical coupling between the two displacement pistons in a device according to one or more embodiments shown and described herein.
FIG. 2C schematically depicts a mechanical coupling between the two displacement pistons in a device according to one or more embodiments shown and described herein.

Further embodiments comprising a mechanical coupling 16 between the displacement pistons 41, 41' are schematically depicted in FIGS. 2A-2C. In one embodiment (FIG. 2A), the displacement pistons 41, 41' are parallel to one another and the mechanical coupling 16 is a pivot arm mechanism. The mechanical coupling 16 may also be a crankshaft mechanism when the displacement pistons 41, 41' are parallel. In another embodiment (FIG. 2B), the displacement pistons 41, 41' are reversely aligned and the mechanical coupling 16 is a rigid rod. In a further embodiment (FIG. 2C), the pressurizing chamber 43 and the evacuation chamber 44 are disposed in a cylinder 46. A displacement piston 41 is moveably arranged in the cylinder 46, and separates the cylinder 46 into inner volumes 45, 45'.

Figure 3:
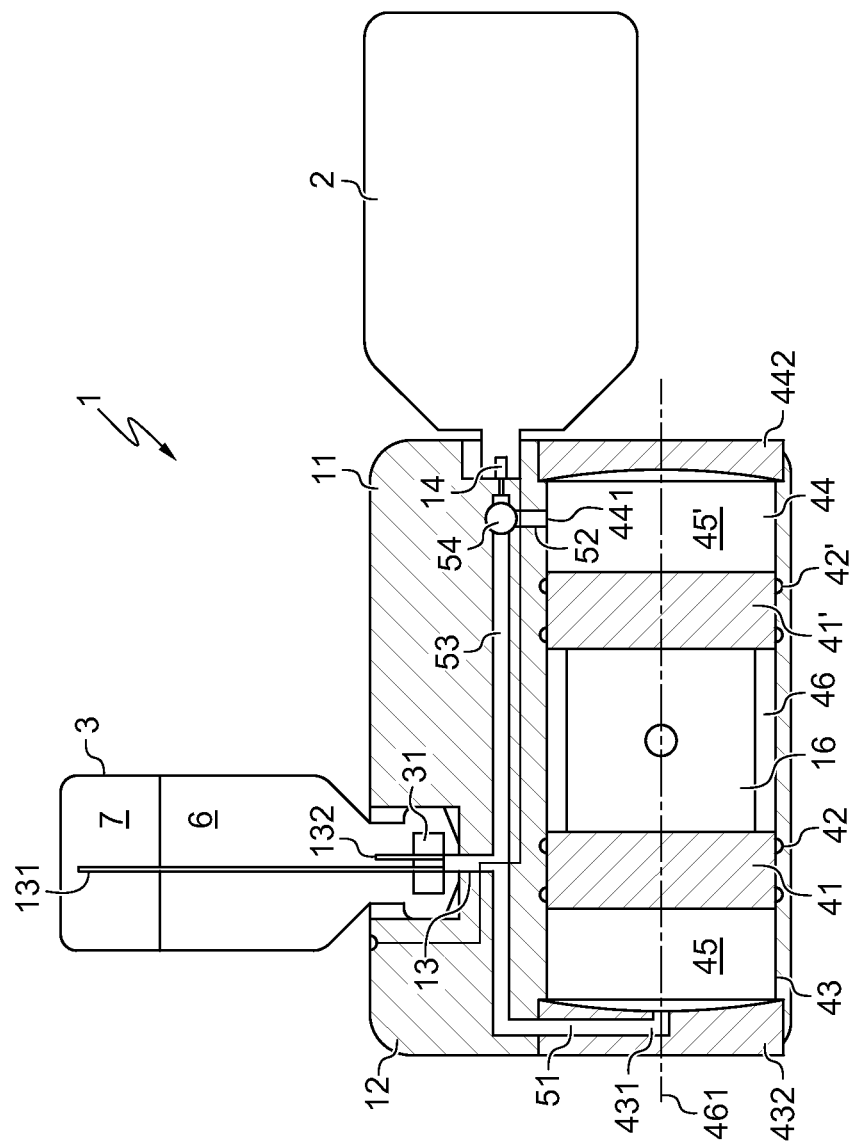
FIG. 3 schematically depicts a cross-section of a device for filling a flexible container according to one or more embodiments shown and described herein.
Figure 4:
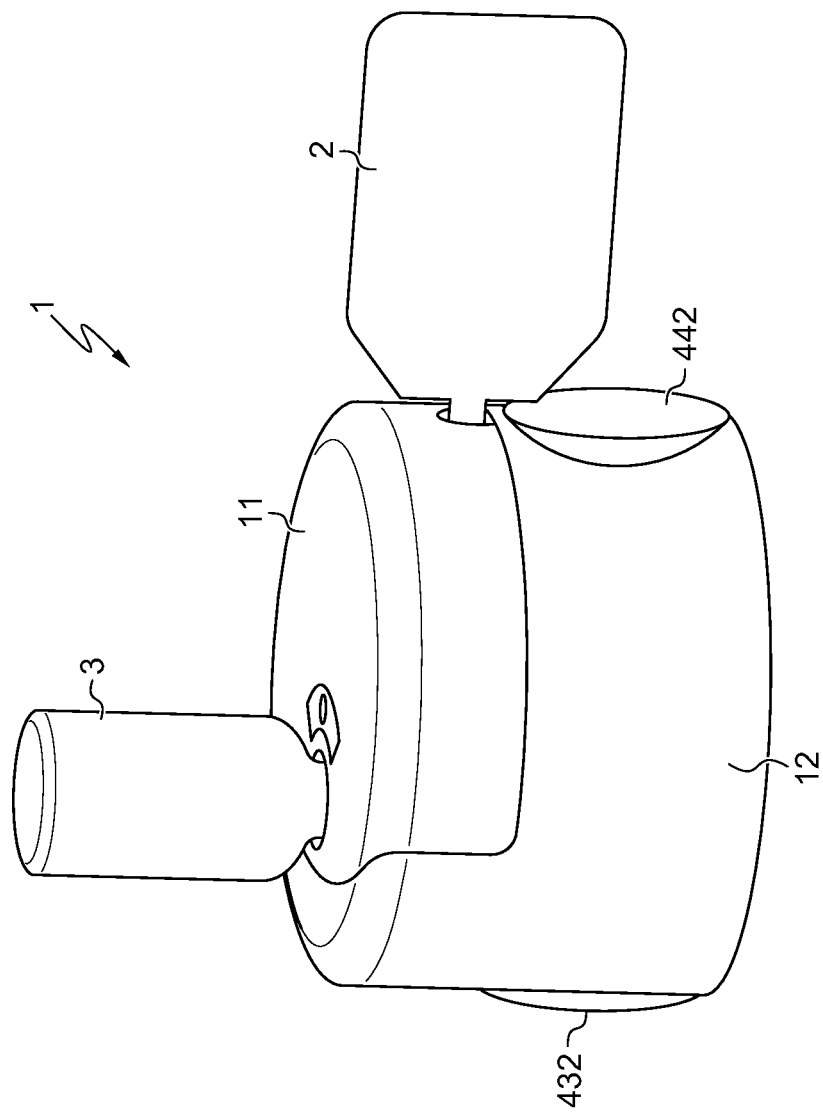
FIG. 4 depicts a perspective view of a device for filling a flexible container according to one or more embodiments shown and described herein.

Referring now to FIGS. 3 and 4, an embodiment of a device 1 for filling a flexible container is depicted. A combined displacement piston structure comprising displacement pistons 41, 41' and a mechanical coupling 16 is slideably movable along a longitudinal axis 461 of the cylinder 46. The pressurizing chamber 43 and the evacuation chamber 44 are disposed within a cylinder 46. Displacement pistons 41, 41' are disposed within the cylinder and rigidly coupled by the mechanical coupling 16. The two ends of the cylinder 46 are sealingly closed with two cover plates 432, 442. For each of the displacement pistons 41, 41', two circumferential sealings 42, 42' provide an airtight closure of the inner volumes 45, 45'.

A pressurizing conduit 51 located in the body of the device 1 leads from an inlet 431 on the concave front face of the pressurizing chamber 43 to the reservoir adapter 13, where it is fluidly connected to a hollow needle 131. A short evacuation conduit 52 connects an outlet 441 in the cylinder wall with a multi-way valve 54, which is also fluidly connected with the container adapter 14 and the transfer conduit 53. The transfer conduit leads from the multi-way valve 54 to the reservoir adapter 13, where it is fluidly connected with another hollow needle 132.

Still referring to FIGS. 3 and 4, in one embodiment, a liquid reservoir 3, for example a reversely mounted vial, is mounted to the reservoir adapter 13 of the device 1. The hollow needles 131, 132 of the reservoir adapter 13 protrude through a septum 31 of the liquid reservoir 3. The length of the first hollow needle 131, which is connected to the pressurizing conduit 51, is configured such that its tip is near the bottom of the liquid reservoir 3. The length of the second hollow needle 132, which is connected to the transfer conduit 53, is configured such that its tip is close to the septum 31. The configuration of the hollow needles 131, 132 reduces the probability that the air that is pressed into the liquid reservoir 3 when it is pressurized will be injected into the liquid 6. The decrease in injected air decreases the probability of air bubble formation and the probability of air bubbles entering the transfer conduit 53 and the flexible container 2.

In the embodiments described herein, the container adapter 14 may be directly connected with the flexible container 2, or connected with the flexible container via a connection element 141 that may be disposable.

An embodiment of the device 1, as depicted in FIGS. 3 and 4, comprises a disposable subunit 11 and a reusable subunit 12 that can be detached from each other. The reusable subunit 12 comprises the pressurizing chamber 43, the evacuation chamber 44 and the displacement pistons 41, 41'. The elements disposed within the reusable subunit do not come into contact with the liquid 6 during operation of the device 1. Therefore, the reusable subunit 12 has a low probability of becoming contaminated by the liquid 6.

The disposable subunit 11 comprises the reservoir adapter 13 for the liquid reservoir 3, the container adapter 14 for the flexible container 2, and the transfer conduit 53. Such parts of the device 1 periodically come into contact with the liquid 6, and thus have to be regularly replaced for hygienic reasons.

In another embodiment comprising a disposable subunit 11 and a reusable subunit 12, the pressure may be automatically equalized between the chambers 43, 44 by detaching one of the subunits 11, 12 from the device 1. For example, when the disposable subunit 11 is detached the displacement pistons 41, 41' can be brought back into the starting position.

In further embodiments, hydrophobic filters may be disposed within the pressurizing conduit 51 and/or the evacuation conduit 52 to prevent any liquid from entering the conduits 51, 52. For example, the hydrophobic filters may be disposed within the disposable subunit 11. Additionally, non-return valves may be utilized in the pressurizing conduit 51 to minimize liquid infiltration.

The displacement pistons 41, 41' can be actuated by any suitable mechanism. Since the space of the cylinder 46 between the displacement pistons 41, 41' may be open, the mechanical coupling 16 may be coupled to an external actuation mechanism or actuator. For example, a lever or arm (not shown) may protrude from the outside into the cylinder 46, and connect to the mechanical coupling 16. In one embodiment, the lever may be actuated by hand. Thusly, a user can manually move the displacement pistons 41, 41' along the longitudinal axis 461 of the cylinder 46.

Figure 5:
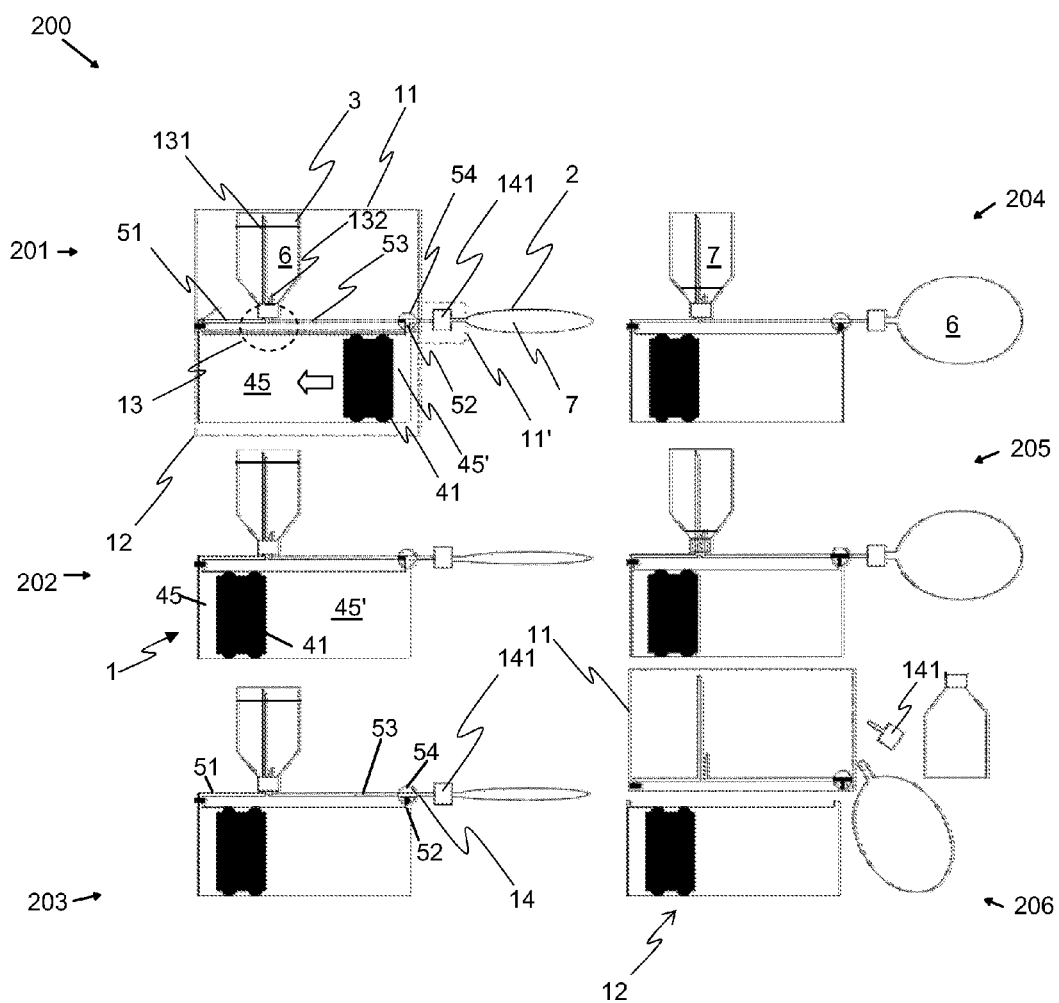
FIG. 5 schematically depicts a method for filling a flexible container according to one or more embodiments shown and described herein.

A method 200 for filling a flexible container 2, according to the present disclosure, is schematically depicted in FIG. 5.

The method 200 comprises, step 201, preparing the device. A liquid reservoir with a liquid 6 such as, a liquid medicament, is connected with the reservoir adapter 13. A displace piston 41 such that the inner volume 45 of the pressurizing chamber 43 is maximized, and the inner volume 45' of the evacuation chamber 44 is minimized. The flexible container 2 is fluidly connected to a disposable connection element 141, which is configured to connect to the container adapter 14. A multi-way valve 54 is switched such that the transfer conduit 53 is interrupted (black marking), and the evacuation conduit 52 is fluidly connected to the flexible container 2. The flexible container 2 may be partially inflated and contain some remaining air 7 inside.

In step 202, the displacement piston 41 is moved to the left, thereby increasing the inner volume 45' of the evacuation chamber 44 and decreasing the inner volume 45 of the pressurizing chamber 43 (FIG. 1). As a result, the remaining air 7 inside of the flexible container 2 is sucked into the evacuation chamber 44 (FIG. 1). The air in the flexible container 2 is nearly completely removed, and the inner pressure in the flexible container 2 is reduced to a minimum. The amount of air in the dead volume of the flexible container 2 is reduced, based on a normal pressure calculation. The air in the inner volume 45 of the pressurizing chamber 43 is simultaneously compressed, and the interior of the liquid reservoir 3 is pressurized via the pressurizing conduit 51.

Subsequently, in step 203 when the displacement piston 41 has reached a maximum position the valve 54 is switched such that that the evacuation conduit 52 is disconnected from the container adapter 14 and flexible container 2. The transfer conduit 53 is fluidly connected with the flexible container 2. The liquid 6 can now flow via the transfer conduit 53 from the liquid reservoir 3 to the flexible container 2. The pressure difference between the liquid reservoir 3 (relatively high) and the flexible container 2 (relatively low, e.g., atmospheric pressure, as long as maximum filling capacity is not reached). To limit the maximum flow speed of the liquid during transfer, such as during the beginning of the transfer, the transfer conduit 53 may be provided with meanders, flow restrictors or capillaries, for example.

The valve 54 may be switched by, for example, a user, or automatic triggering. In one embodiment, the valve is automatically switched when the displacement piston 41 reaches a certain position. Further embodiments comprise a locking mechanism that locks the displacement piston 41 at a position, such as, for example, the maximum position. The locking mechanism of the piston may also be used as the trigger for switching the valve 54. Furthermore, the locking mechanism may be releasable for reusing the device.

In another embodiment, the locking mechanism may only be released when a used, disposable subunit 11 has been removed. Thus, the risk of an accidental contamination of the reusable subunit 12 due to an operating error is further reduced.

Still referring to FIG. 5, in step 204, the valve 54 remains in its current state until the desired filling level of the flexible container 2 has been reached, or the liquid reservoir 3 has been emptied. While the liquid reservoir 3 and the flexible container 2 are depicted in FIG. 5 as having the same volume, it is noted that the volume of the liquid reservoir 3 may be considerably larger than the volume of the flexible container 2 to be filled. Therefore, the contents of the liquid reservoir 3 may be sufficient to fill several of the flexible containers 2. For example, a common insulin vial contains 10 ml of insulin solution, which may be sufficient to fill up three to five commonly available flexible containers for use in an insulin infusion pump device.

In step 205, the valve 54 is switched again, and both the evacuation conduit 52 and the transfer conduit 53 are disconnected from the container adapter 14.

In step 206, the filled flexible container 2 is detached from the connection element 141, and may then be connected to an infusion pump device. The connection element 141, which may be disposable, is removed from the container adapter 14. The liquid reservoir 3 may be removed, for example, when it is empty, from the reservoir adapter 13. The disposable subunit 11 is also removed from the reusable subunit 12 of the device 1.

In another embodiment of the present disclosure, the connection element 141 may remain connected to the flexible container 2, and may be used for liquidly connecting the container with an infusion pump device.

The reservoir adapter 13 may also comprise a mechanism that prevents the removal of the liquid reservoir 3 from the reservoir adapter 13. For example, the liquid reservoir 3 may not be removed when the disposable subunit 11 is connected to the reusable subunit 12. The liquid reservoir 3 may be permanently coupled to the reservoir adapter 13 after they are connected, such that the liquid reservoir 3 and the disposable subunit 11 have to be disposed together.

Referring again to FIGS. 1 and 5, the displacement piston 41 is set back to the starting position, step 201, prior to the next use. For example, the locking mechanism of the displacement piston 41 may be released. In one embodiment, a spring element is used to move the displacement piston 41 back to the starting position. A new disposable subunit 11 may then be attached to the subunit 12 to prepare the device 1 for use. In a further embodiment, the displacement pistons 41, 41' may be set back to the starting position by manually operating the actuation mechanism of the displacement pistons 41, 41', for example with a lever and the like.

A further embodiment of a device 1 according to the present disclosure is schematically depicted in FIG. 6.

The multi-way valve 54 is disposed near the center of the device 1 and the reservoir adapter 13 to reduce the volume of the transfer conduit 53 and the potential amount of air remaining in the conduits 51, 52, 53.

A bubble trap 56 is disposed adjacent to the valve 54. The bubble trap 56, or bubble filter, is configured to remove air bubbles from the liquid stream, or retain them in the bubble trap 56. An example of a bubble trap 56 is disclosed in the European application No. 09155216 assigned to the applicants. Said application is hereby incorporated by reference in its entirety as part of the present disclosure.

Embodiments described herein comprise a degassing membrane 55 disposed upstream of the bubble trap 56 arranged in the wall of the conduit 53. The degassing membrane 55 is configured to allow any air remaining in the conduit 53 to permeate through the degassing membrane 55, while any liquid 6 is retained in the conduit 53. In one embodiment, the liquid reservoir 3 is pressurized and a certain time period is allowed to pass prior to switching the valve 54 to connect the transfer conduit 53 to the flexible container 2. When the liquid reservoir 3 is pressurized to a pressure greater than the ambient air pressure, air in the transfer conduit 53 will escape through the degassing membrane 55 and will be replaced in the transfer conduit 53 by liquid 6.

Referring still to FIG. 6, an embodiment of the evacuation conduit 52 comprises two segments 52", 52'. A first segment 52" located in the structure of the device leads from the valve 54 to a wall of the cylinder 46. A second segment 52' is located in the displacement piston 41', and leads from the outlet 441 located on the front face of the displacement piston 41' to an opening located between the two circumferential sealings 42 of the displacement piston 41'. The displacement piston 41' and the evacuation conduit 52 act as a gate valve because the evacuation conduit 52 is closed as long as the openings of the two segments 52", 52' do not overlap. As a consequence of the gate valve-like nature, air in the flexible container 2 is not sucked into the evacuation chamber 44 continuously during the shifting of the displacement pistons 41, 41'. Air in the flexible container 2 is sucked into the evacuation chamber 44 only when the displacement pistons 41, 41' have come to the maximum position for inner volume 45' (left-most position in FIG. 6). At this position, the two segments 52", 52' of the evacuation conduit 52 are the fluidly connected, and the valve 54 has been switched to connect the evacuation conduit 52 to the flexible container 2. Thusly, the two functions of pressurizing the liquid reservoir 3 and evacuating the flexible container 2 may occur at different points of time, which may reduce the number of valves in the device 1.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

What is claimed is:

1. A device for filling a flexible liquid medicament container with a liquid from a liquid reservoir, the device for filling a liquid medicament container comprising:

a pressurizing chamber;

an evacuation chamber;

a first displacement piston sealingly and slideably arranged within the pressurizing chamber, wherein the first displacement piston defines a first inner volume within the pressurizing chamber;

a second displacement piston sealingly and slideably arranged within the evacuation chamber, wherein the second displacement piston defines a second inner volume within the evacuation chamber;

a reservoir adapter fluidly connected to the first inner volume of the pressurizing chamber and which connects to the liquid reservoir and allows an increased pressure to be transferred from the pressurizing chamber, containing a pressurizing gas, to the interior of the liquid reservoir thereby allowing the gas to contact the liquid within the liquid reservoir; and a valve that fluidly connects the flexible liquid medicament container to either the interior of the liquid reservoir via the reservoir adapter, or the second inner volume of the evacuation chamber.

2. The device for filling a liquid medicament container of claim 1, wherein the valve is a multi-way valve that fluidly and switchably connects the flexible liquid medicament container between the interior of the liquid reservoir, via the reservoir adapter, and the second inner volume of the evacuation chamber.

3. The device for filling a liquid medicament container of claim 2, wherein the multi-way valve is actuated by a movement of the first displacement piston, the second displacement piston, an actuation mechanism, an actuator, or a locking mechanism.

4. The device for filling a liquid medicament container of claim 1, wherein the valve is a first valve that fluidly connects the flexible liquid medicament container to the interior of the liquid reservoir via the reservoir adapter, and said device further comprises a second valve that fluidly connects the flexible liquid medicament container to the second inner volume of the evacuation chamber.

5. The device for filling a liquid medicament container of claim 1, further comprising a pressurizing conduit that is fluidly connected to the first inner volume of the pressurizing chamber, and the reservoir adapter is fluidly connected directly to the pressurizing conduit.

6. The device for filling a liquid medicament container of claim 5, further comprises one of a hydrophobic filter disposed within the pressurizing conduit, and a non-return valve provided in the pressurizing conduit to minimize liquid infiltration.

7. The device for filling a liquid medicament container of claim 1, further comprises a transfer conduit fluidly connected directly to the reservoir adapter.

8. The device for filling a liquid medicament container of claim 7, further comprising a degassing membrane which removes a gas from the transfer conduit.

9. The device for filling a liquid medicament container of claim 1, further comprising a container adapter for fluidly connecting the flexible liquid medicament container to the device, an evacuation conduit that is fluidly connected to the second inner volume of the evacuation chamber and fluidly connected directly to the container adapter, and a transfer conduit fluidly connected directly to the reservoir adapter and the container adapter.

10. The device for filling a liquid medicament container of claim 9, further comprising one of a bubble trap disposed in the transfer conduit between the reservoir adapter and the container adapter, a check valve disposed in the transfer conduit between the reservoir adapter and the container adapter, a capillary segment disposed in the transfer conduit between the reservoir adapter and the container adapter, a flow restrictor disposed in the transfer conduit between the reservoir adapter and the container adapter, and a hydrophobic filter disposed within the evacuation conduit.

11. The device for filling a liquid medicament container of claim 1, wherein the first displacement piston is coupled to the second displacement piston, such that as the first inner volume is decreased the second inner volume is increased, and as the first inner volume is increased the second inner volume is decreased.

12. The device for filling a liquid medicament container of claim 1, wherein:

a single displacement piston comprises the first displacement piston and the second displacement piston;

the pressurizing chamber and the evacuation chamber are disposed in a closed cylinder separated by the single displacement piston; and the single displacement piston is displaceable along a longitudinal axis of the closed cylinder.

13. The device for filling a liquid medicament container of claim 1, wherein:

the pressurizing chamber and the evacuation chamber are disposed in a closed cylinder separated by the first displacement piston and the second displacement piston;

the first displacement piston is rigidly connected to the second displacement piston; and the first displacement piston and the second displacement piston are displaceable along a longitudinal axis of the closed cylinder.

14. The device for filling a liquid medicament container of claim 1 further comprising a first subunit and a second subunit, wherein:

the first subunit comprises the reservoir adapter;

the second subunit comprises the pressurizing chamber, the evacuation chamber, the first displacement piston and the second displacement piston; and the first subunit is detachable from the second subunit.

15. The device for filling a liquid medicament container of claim 1, wherein:

the reservoir adapter comprises a first hollow needle and a second hollow needle, both which is configured to penetrate a septum of the liquid reservoir;

the first hollow needle is parallel to the second hollow needle;

the first hollow needle is fluidly connected to the pressurizing conduit; and the second hollow needle is fluidly connected to the evacuation conduit.

16. The device for filling a liquid medicament container of claim 1, further comprising at least one of a gate valve disposed within the pressurizing conduit, wherein the gate valve disposed within the pressurizing conduit temporarily interrupts the pressurizing conduit depending on a position of the first displacement piston and/or the second displacement piston, and a gate valve disposed within the evacuation conduit, wherein the gate valve disposed within the evacuation conduit temporarily interrupts the evacuation conduit depending on a position of the first displacement piston and/or the second displacement piston.

17. The device for filling a liquid medicament container of claim 1, wherein the first displacement piston and/or the second displacement piston is manually operated, and wherein a single stroke of the first displacement piston or the second displacement piston is configured to fill the flexible container.

18. A method for filling a flexible liquid medicament container with a liquid from a liquid reservoir, the method for filling the flexible liquid medicament container comprising:

attaching the flexible liquid medicament container to a device which comprises:
- a pressurizing chamber,
- an evacuation chamber,
- a first displacement piston sealingly and slideably arranged within the pressurizing chamber, wherein the first displacement piston defines a first inner volume within the pressurizing chamber,
- a second displacement piston sealingly and slideably arranged within the evacuation chamber, wherein the second displacement piston defines a second inner volume within the evacuation chamber, and
- a reservoir adapter fluidly connected to the first inner volume of the pressurizing chamber and which connects to the liquid reservoir and allows an increased pressure to be transferred from the pressurizing chamber, containing a pressurizing gas, to the interior of the liquid reservoir thereby allowing the gas to contact the liquid within the liquid reservoir;

fluidly connecting the flexible liquid medicament container to the second inner volume of the evacuation chamber;

evacuating the flexible liquid medicament container via moving the second displacement piston within the evacuation chamber;

pressurizing the liquid reservoir via moving the first displacement piston within the pressurizing chamber;

fluidly connecting the flexible liquid medicament container to the reservoir adapter; and transferring a liquid from the liquid reservoir to the flexible liquid medicament container with a pressure difference between the reservoir and the container.

19. The method for filling a flexible liquid medicament container of claim 18, wherein moving the first displacement piston decreases the inner volume of the pressurizing chamber.

20. The method for filling a flexible liquid medicament container of claim 18, wherein moving the second displacement piston increases the inner volume of the evacuation chamber.

* * * * *